(12) United States Patent
Heck et al.

(10) Patent No.: US 7,867,282 B2
(45) Date of Patent: *Jan. 11, 2011

(54) MODULAR IMPLANT SYSTEM AND METHOD WITH DIAPHYSEAL IMPLANT AND ADAPTER

(75) Inventors: Robert K. Heck, Memphis, TN (US); Stephen A. Hazebrouck, Winona Lake, IN (US)

(73) Assignee: Depuy Products, Inc., Warsaw, IN (US)

( * ) Notice: Subject to any disclaimer, the term of this patent is extended or adjusted under 35 U.S.C. 154(b) by 1020 days.

This patent is subject to a terminal disclaimer.

(21) Appl. No.: 11/302,571

(22) Filed: Dec. 14, 2005

(65) Prior Publication Data

US 2006/0167560 A1 Jul. 27, 2006

Related U.S. Application Data

(60) Provisional application No. 60/637,015, filed on Dec. 17, 2004, provisional application No. 60/731,999, filed on Oct. 31, 2005, provisional application No. 60/732,402, filed on Oct. 31, 2005.

(51) Int. Cl.
*A61F 2/30* (2006.01)
*A61F 2/36* (2006.01)

(52) U.S. Cl. ............... 623/23.46; 623/20.36; 623/22.42; 623/23.15; 623/23.21; 606/62; 606/63

(58) Field of Classification Search ................ None
See application file for complete search history.

(56) References Cited

U.S. PATENT DOCUMENTS

| | | | |
|---|---|---|---|
| 3,605,123 A | 9/1971 | Hahn | |
| 3,848,272 A | 11/1974 | Noiles | |
| 4,219,893 A | 9/1980 | Noiles | |
| 4,301,553 A | 11/1981 | Noiles | |
| 4,384,373 A | 5/1983 | Sivash | |
| 4,502,160 A | 3/1985 | Moore et al. | |
| 4,676,797 A | 6/1987 | Anapliotis et al. | |
| 4,695,283 A * | 9/1987 | Aldinger | 623/23.24 |
| 4,787,907 A | 11/1988 | Carignan | |

(Continued)

FOREIGN PATENT DOCUMENTS

WO    WO 02/47585 A1    6/2002

OTHER PUBLICATIONS

BIOMET, Orthopaedic Salvage System Overview.

(Continued)

*Primary Examiner*—David H Willse
*Assistant Examiner*—Javier G Blanco

(57) ABSTRACT

A modular implant system includes a set of anatomically-designed diaphyseal fitting and filling modular implant components and adapters for connection to another implant component such as a modular articular component, a segmental component or an intercalary component. The other end of each diaphyseal component is a tapered porous surface. The tapered porous surface is received with a tapered bore in the bone diaphysis that is prepared to match the size and shape of the tapered porous surface. The diaphyseal implant is easy to insert and remove, does not bind before fully seating, and is designed to prevent stress shielding. The diaphyseal sleeve eliminates the long lever arm created when fixation occurs only at the tip of the stem, and should therefore eliminate related stem loosening.

5 Claims, 9 Drawing Sheets

U.S. PATENT DOCUMENTS

| | | | |
|---|---|---|---|
| 4,790,852 A | 12/1988 | Noiles | |
| 4,822,366 A | 4/1989 | Bolesky | |
| 4,846,839 A * | 7/1989 | Noiles | 623/23.46 |
| 4,938,768 A | 7/1990 | Wu | |
| 5,032,130 A | 7/1991 | Schelhas et al. | |
| 5,080,685 A | 1/1992 | Bolesky et al. | |
| 5,152,796 A | 10/1992 | Slamin | |
| 5,181,928 A | 1/1993 | Bolesky et al. | |
| 5,286,260 A | 2/1994 | Bolesky et al. | |
| 5,330,534 A | 7/1994 | Herrington et al. | |
| 5,358,524 A | 10/1994 | Richelsoph | |
| 5,370,706 A | 12/1994 | Bolesky et al. | |
| 5,653,765 A | 8/1997 | McTighe et al. | |
| 5,658,349 A | 8/1997 | Brooks et al. | |
| 5,755,805 A * | 5/1998 | Whiteside | 623/23.24 |
| 5,782,921 A | 7/1998 | Colleran et al. | |
| 5,824,097 A | 10/1998 | Gabriel et al. | |
| 5,876,459 A | 3/1999 | Powell | |
| 5,906,644 A | 5/1999 | Powell | |
| 6,071,311 A | 6/2000 | O'Neil et al. | |
| 6,102,956 A | 8/2000 | Kranz | |
| 6,171,342 B1 | 1/2001 | O'Neil | |
| 6,214,052 B1 | 4/2001 | Burkinshaw | |
| 6,264,699 B1 | 7/2001 | Noiles et al. | |
| 6,428,578 B2 | 8/2002 | White | |
| 6,527,807 B1 | 3/2003 | O'Neil et al. | |
| 6,613,092 B1 * | 9/2003 | Kana et al. | 623/20.15 |
| 6,692,530 B2 | 2/2004 | Doubler et al. | |
| 6,712,858 B1 | 3/2004 | Grundei et al. | |
| 6,723,129 B2 | 4/2004 | Dwyer et al. | |
| 6,755,862 B2 * | 6/2004 | Keynan | 623/16.11 |
| 6,786,931 B2 | 9/2004 | Hazebrouck | |
| 6,824,566 B2 | 11/2004 | Kana et al. | |
| 6,866,683 B2 | 3/2005 | Gerbec et al. | |
| 6,875,239 B2 | 4/2005 | Gerbec et al. | |
| 6,902,583 B2 | 6/2005 | Gerbec et al. | |
| 7,175,664 B1 | 2/2007 | Lakin | |
| 7,507,256 B2 | 3/2009 | Heck et al. | |
| 2003/0204267 A1 | 10/2003 | Hazebrouck | |
| 2004/0162621 A1 * | 8/2004 | Crofford | 623/22.43 |
| 2004/0193267 A1 | 9/2004 | Jones | |
| 2004/0193268 A1 | 9/2004 | Hazebrouck | |
| 2005/0071014 A1 * | 3/2005 | Barnett et al. | 623/19.14 |
| 2005/0107794 A1 | 5/2005 | Hazebrouck | |
| 2005/0107883 A1 | 5/2005 | Goodfried | |
| 2006/0030945 A1 | 2/2006 | Wright | |
| 2006/0041317 A1 | 2/2006 | Hazebrouck | |
| 2006/0167555 A1 | 7/2006 | Heck et al. | |

OTHER PUBLICATIONS

DE PUY, Reconstructive/Revision Products, pp. 182 & 184.
DePUY Orthopaedics, Inc., M.B.T. Revision Tray, 2004, DePuy Orthopaedics, Inc., Warsaw, Indiana.
DePUY Orthopaedics, Inc., S-ROM NOILES Rotating Hinge, 2002, DePuy Orthopaedics, Inc., Warsaw, Indiana.
International Search Report dated May 11, 2006, for corresponding PCT Application PCT/US05/45197.
Restriction Requirement—May 12, 2009—U.S. Appl. No. 11/302,804.
Non-Final Rejection—Oct. 2, 2009—U.S. Appl. No. 11/302,804.
Non-Final Rejection—Oct. 11, 2007—US Pat. 7507256 (Scanned copy attached due to not being found in pair).
Final Rejection—Jul. 14, 2008—US Pat. 7507256.
Notice of Allowance—Nov. 18, 2008—US Pat. 7507256.
Japanese Search Report for Corresponding Patent Application No. 2007-546849, Dated Apr. 27, 2010, 4 Pages.
Japanese Search Report for Corresponding Patent Application No. 2007-546850, Dated Apr. 27, 2010, 2 Pages.
Japanese Search Report for Corresponding Patent Application No. 2007-546814, Dated Apr. 27, 2010, 2 Pages.

* cited by examiner

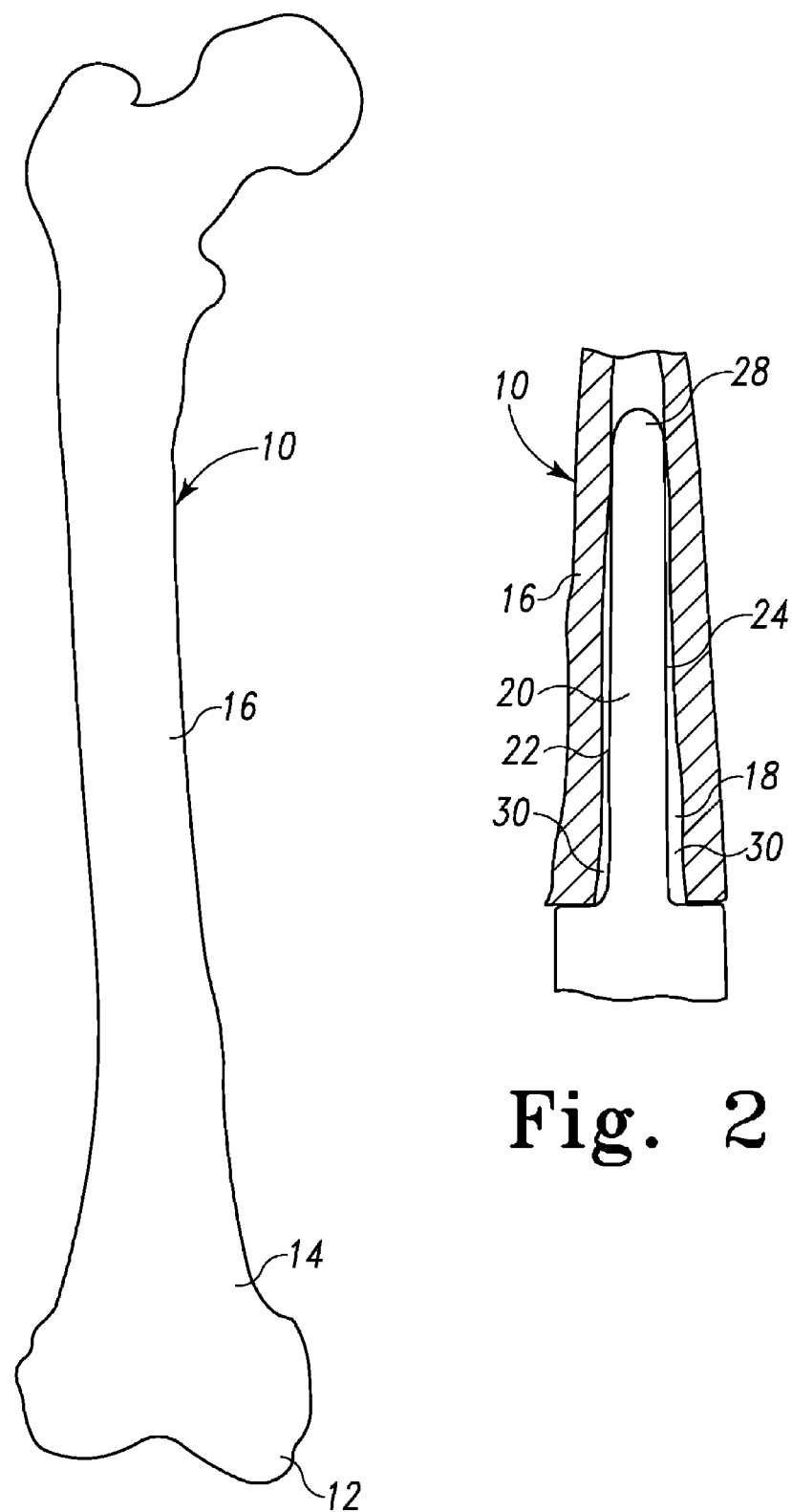

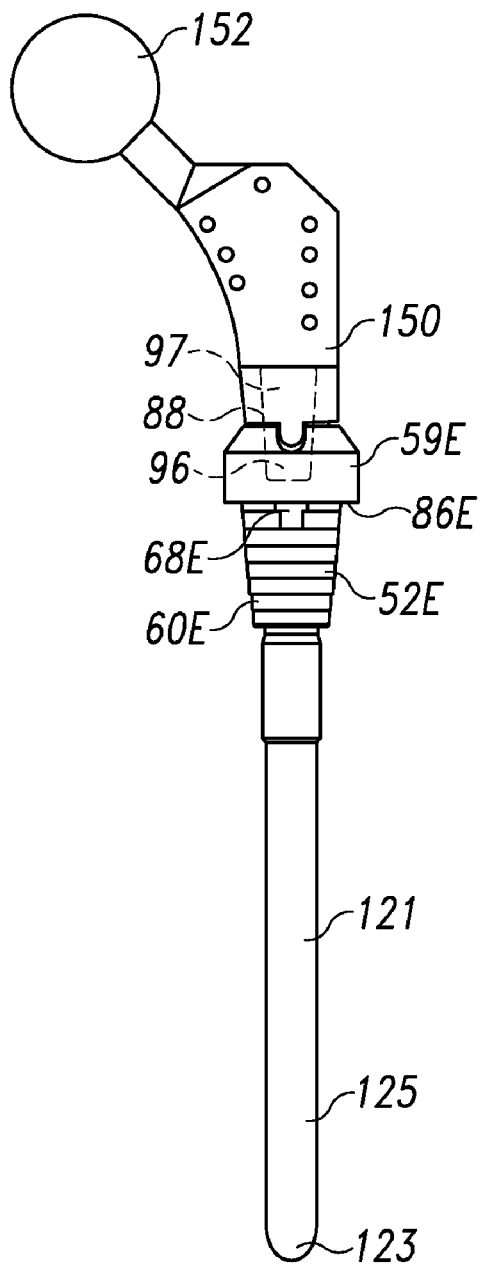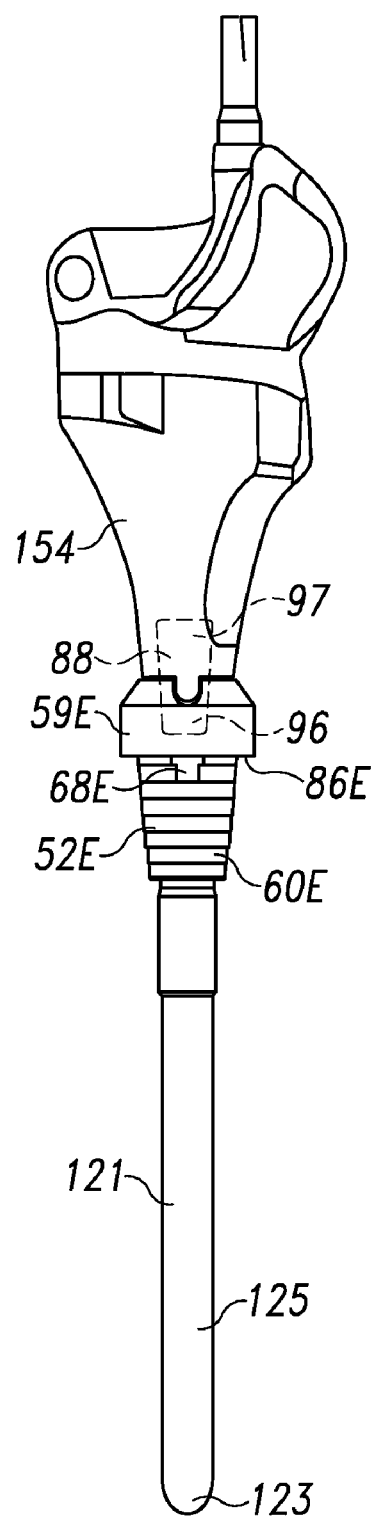
Fig. 12
Fig. 13

MODULAR IMPLANT SYSTEM AND METHOD WITH DIAPHYSEAL IMPLANT AND ADAPTER

CROSS-REFERENCE TO RELATED APPLICATIONS

The present invention claims priority to U.S. Provisional Patent Application Ser. No. 60/637,015, filed on Dec. 17, 2004 by Robert K. Heck and Stephen A. Hazebrouck and entitled "Modular Implant System and Method with Diaphyseal Implant," U.S. Provisional Patent Application Ser. No. 60/731,999, filed on Oct. 31, 2005 by Robert K. Heck and Stephen A. Hazebrouck, and entitled "Modular Diaphyseal and Collar Implant," and U.S. Provisional Patent Application Ser. No. 60/732,402, filed on Oct. 31, 2005 by Robert K. Heck and Stephen A. Hazebrouck and entitled "Modular Implant System and Method with Diaphyseal Implant and Adapter," all of which are incorporated by reference herein in their entireties.

BACKGROUND OF THE INVENTION

The present invention relates generally to prosthetic joints and, more particularly, to modular orthopaedic lower extremity implant systems.

The knee joint basically consists of the bone interface of the distal end of the femur and the proximal end of the tibia. Appearing to cover or at least partially protect this interface is the patella which is a sesamoid bone within the tendon of the long muscle (quadriceps) on the front of the thigh. This tendon inserts into the tibial tuberosity and the posterior surface of the patella is smooth and glides over the femur.

The distal femur is configured with two knob like processes (the medial condyle and the lateral condyle) which are substantially smooth and which articulate with the medial plateau and the lateral plateau of the tibia, respectively. The plateaus of the tibia are substantially smooth and slightly cupped thereby providing a slight receptacle for receipt of the femoral condyles.

The hip joint consists of the bone interface of the proximal end of the femur and the acetabulum of the hipbone. The proximal femur is configured with a ball-shaped head, which is received within and articulates against the cup-shaped cavity defined by the acetabulum.

When the knee or hip joint is damaged whether as a result of an accident or illness, a prosthetic replacement of the damaged joint may be necessary to relieve pain and to restore normal use to the joint. Typically the entire joint is replaced by means of a surgical procedure, which involves removal of the surfaces of the corresponding damaged bones and replacement of these surfaces with prosthetic implants. This replacement of a native joint of the leg with a prosthetic joint is referred to as primary total-knee arthroplasty and primary total-hip arthroplasty.

On occasion, the primary prosthesis fails. Failure can result from many causes, including wear, aseptic loosening, osteolysis, ligamentous instability, arthrofibrosis and patellofemoral complications. When the failure is debilitating, revision surgery may be necessary. In a revision, the primary prosthesis is removed and replaced with components of a revision prosthetic system.

Implant systems for both primary and revision applications are available from a variety of manufacturers, including DePuy Orthopaedics, Inc. of Warsaw, Ind. DePuy and others offer several different systems for both primary and revision applications. For example, DePuy Orthopaedics offers the P.F.C. SIGMA® Knee System, the LCS® Total Knee System, and the S-ROM Modular Total Knee System. Each of these orthopaedic knee systems includes several components, some appropriate for use in primary knee arthroplasty and some appropriate for use in revision surgery.

DePuy Orthopaedics also offers other orthopaedic implant systems for other applications. One such system is the LPS System. The LPS System is provided for use in cases of neoplastic diseases (e.g., osteosarcomas, chrondrosarcomas, giant cell tumors, bone tumors) requiring extensive resections and replacements of the proximal and/or distal femur, severe trauma, disease (e.g., avascular necrosis, osteoarthritis and inflammatory joint disease requiring extensive resection and replacement of the proximal and/or distal femur, and resection cases requiring extensive resection and replacement of the proximal, distal or total femur or proximal tibia (e.g., end-stage revision). Any of these conditions or a combination thereof can lead to significant amounts of bone loss. The LPS System provides components that can replace all or significant portions of a particular bone, such as the femur or tibia. The DePuy LPS System is described more fully in U.S. patent application Ser. No. 10/135,791, entitled "Modular Limb Preservation System", filed Apr. 30, 2002 by Hazebrouck et al., U.S. Pat. Publication No. US2003/0204267A1 (published Oct. 30, 2003) which is incorporated by reference herein in its entirety. Other companies also offer systems for similar indications.

The LPS system provides a comprehensive set of modular implants capable of addressing a wide range of orthopaedic conditions. Components of the LPS system can be combined in a variety of ways to account for variations in patient anatomy and differences in the amount of native bone remaining. As disclosed in U.S. Pat. Publication No. US2003/0204267A1, the modular components can be combined to replace the proximal or distal femur, total femur, proximal tibia or the mid-shaft of a long bone. Similar systems can be used with other long bones, such as the bones of the upper arm.

Many of the combinations of components possible with the LPS system include stem components that are configured for implantation within the intramedullary canal of the remaining bone. Metaphyseal sleeves are available for use in the LPS system, as disclosed, for example, in U.S. Pat. Publication No. US2005/0107883A1, entitled "Modular Implant System with Fully Porous Coated Sleeve" (filed on Apr. 2, 2004 by Goodfried, Hazebrouck, Lester and Brown), which is incorporated by reference herein in its entirety. However, in some instances, the stem components must be used with implant components that have replaced the entire articulating portion of the bone and the metaphysis of the bone. In some indications, the remaining native bone comprises the diaphysis or shaft of the long bone, and a metaphyseal sleeve cannot be used.

An example of a long bone is illustrated in FIG. 1; in FIG. 1, the bone 10 is the femur. FIG. 2 illustrates the femur of FIG. 1 after the distal articulating end 12 and metaphysis 14 of the bone 10 have been removed due to neoplastic disease, trauma, disease or as part of an end-stage revision. The diaphysis of the bone is illustrated at 16 in FIGS. 1-2.

As shown in FIG. 2, the intramedullary canal 18 of the diaphysis 16 of the long bone 10 generally tapers, while the implant stem extensions 20 generally have parallel sides, such as those shown at 22, 24. As a result, the implant stem extension 20 frequently contacts the native bone tissue at the free end or tip 28 of the stem extension 20, while leaving gaps 30 along much of the length of the stem extension 20. Although these gaps 30 could be filled with bone cement, for optimal fixation it is desirable to use porous coated stem extensions. Such porous coated stem extensions tend to bind before becoming fully seated. Consequently, in cases where the stem extension is porous coated to encourage bone ingrowth, the bone ingrowth is frequently limited to the free end 28 of the stem. With bone ingrowth limited to the free end of the stem extension, there is stress shielding of the bone surrounding the remainder of the stem extension, and a long lever arm is created; both of these effects can lead to early loosening of the implant. Additionally, when significant ingrowth does occur and the stem extension must subsequently be removed, the procedure can be difficult.

SUMMARY OF THE INVENTION

The present invention addresses the need for an implant system that can be effectively used in the diaphyseal region of a long bone and for a surgical method for implanting a system in the diaphyseal region of a long bone.

In one aspect, the present invention addresses this need by providing a diaphyseal implant component comprising a first end with a bore, a second end with a bore that is co-axial with the bore at the first end, a longitudinal axis extending from the first end to the second end, a collar portion and a porous tapered outer surface. The longitudinal axis extends through the bores at the first end and second end. The collar portion is between the first end and the second end and surrounds at least a portion of the bore at the first end. The collar portion includes an annular surface disposed perpendicular to the longitudinal axis of the implant component. The porous tapered outer surface is adjacent to the annular surface of the collar and extends toward the second end of the implant. The porous tapered outer surface has a maximum outer diameter nearest the annular surface of the collar and a minimum outer diameter at the second end of the implant component. The annular surface of the collar has an outer diameter greater than the maximum outer diameter of the porous tapered outer surface.

In another aspect, the present invention addresses this need by providing an orthopaedic implant kit for replacing a portion of a long bone, the long bone having an articulation portion, a diaphysis and an intramedullary canal. The kit includes a plurality of modular articulation components, a plurality of modular stems, an adapter and a plurality of modular diaphyseal implant components. The modular articulation components are shaped and sized to replace the articulation portion of the long bone. Each modular articulation component includes a tapered bore. The modular stems are shaped to be received in the intramedullary canal of the long bone. Each stem has a free end and an opposite end capable of being connected to another implant component. The adapter has a tapered end sized and shaped to be received in the tapered bore of a selected articulation component for connecting the adapter to the articulation component. The adapter also has a second tapered end. The diaphyseal implant components are capable of being connected to the modular stems. Each diaphyseal implant component has a first end, a second end, a longitudinal axis extending between the first end and the second end, a porous tapered outer surface and a collar. The first end of each diaphyseal implant component has a tapered bore sized and shaped to receive the second tapered end of the adapter for connecting the diaphyseal implant component to one end of the adapter. Each diaphyseal implant component also has a second end for connection to a selected modular stem. The porous tapered surface of each diaphyseal implant component has a minimum outer dimension at the second end and a maximum outer dimension positioned between the first end and the second end. The collar is adjacent to the porous tapered outer surface. The collar includes an annular surface adjacent to the porous tapered outer surface. The annular surface is transverse to the longitudinal axis of the diaphyseal implant component.

In another aspect, the present invention provides a method of replacing a portion of a long bone, the long bone having an articulation portion, a diaphysis, an intramedullary canal and a periosteum. A plurality of modular bone replacement components shaped and sized to replace a portion of the long bone are provided; each modular bone replacement component including a tapered bore. A plurality of modular stems to be received in the intramedullary canal of the long bone are provided; each stem has a free end and an opposite end capable of being connected to another implant component. An adapter having a tapered end sized and shaped to be received in the tapered bore of a bone replacement component is provided; the adapter further comprises a second tapered end. A plurality of modular diaphyseal implant components capable of being connected to the modular stems are provided. Each diaphyseal implant component includes a first end having a tapered bore sized and shaped to receive the second tapered end of the adapter for connecting the diaphyseal component to one end of the adapter. Each diaphyseal implant component also includes a second end for connection to a selected modular stem. A longitudinal axis extends between the first end and the second end. Each diaphyseal implant component has a porous tapered outer surface having a minimum outer dimension at the second end and a maximum outer dimension positioned between the first end and the second end. Each diaphyseal implant component also has a collar adjacent to the porous tapered outer surface. The collars include a porous cylindrical surface surrounding the longitudinal axis of the diaphyseal implant component. The bone is resected to remove a portion of the bone and leave at least a portion of the diaphysis of the bone. A tapered bore is prepared in the diaphysis of the bone. A stem component, diaphyseal component and bone replacement component are selected. An implant assembly is made by connecting the selected stem component to the selected diaphyseal component, inserting one end of the adapter into the tapered bore of the selected diaphyseal component and inserting the other end of the adapter into the tapered bore of the selected bone replacement component. The implant assembly is implanted so that the stem component is received in the intramedullary canal, a substantial part of the diaphyseal component is received in the tapered bore in the diaphysis of the bone and the collar is exposed outside of the bone.

BRIEF DESCRIPTION OF THE DRAWINGS

FIG. 1 is an anterior view of a left femur;

FIG. 2 is a cross-section of a portion of the diaphysis of the femur of FIG. 1, shown with a stem extension received in the intramedullary canal of the femur;

FIG. 12 is a side view of a proximal femoral implant assembly including one of the diaphyseal implant components and adapter of FIGS. 3-4;

FIG. 13 is a perspective view of a proximal tibial implant assembly including one of the diaphyseal implant components and adapter of FIGS. 3-4;

DETAILED DESCRIPTION

A modular orthopaedic knee implant system incorporating the principles of the present invention is illustrated in the accompanying drawings. The illustrated modular orthopaedic knee implant system includes components of several existing orthopaedic knee implant systems, along with new components that provide the orthopaedic-surgeon with greater flexibility in selecting the appropriate components to suit the needs of an individual patient. These patient needs can include factors such as individual anatomy and the condition of the native bone tissue.

Figures 3, 3A:
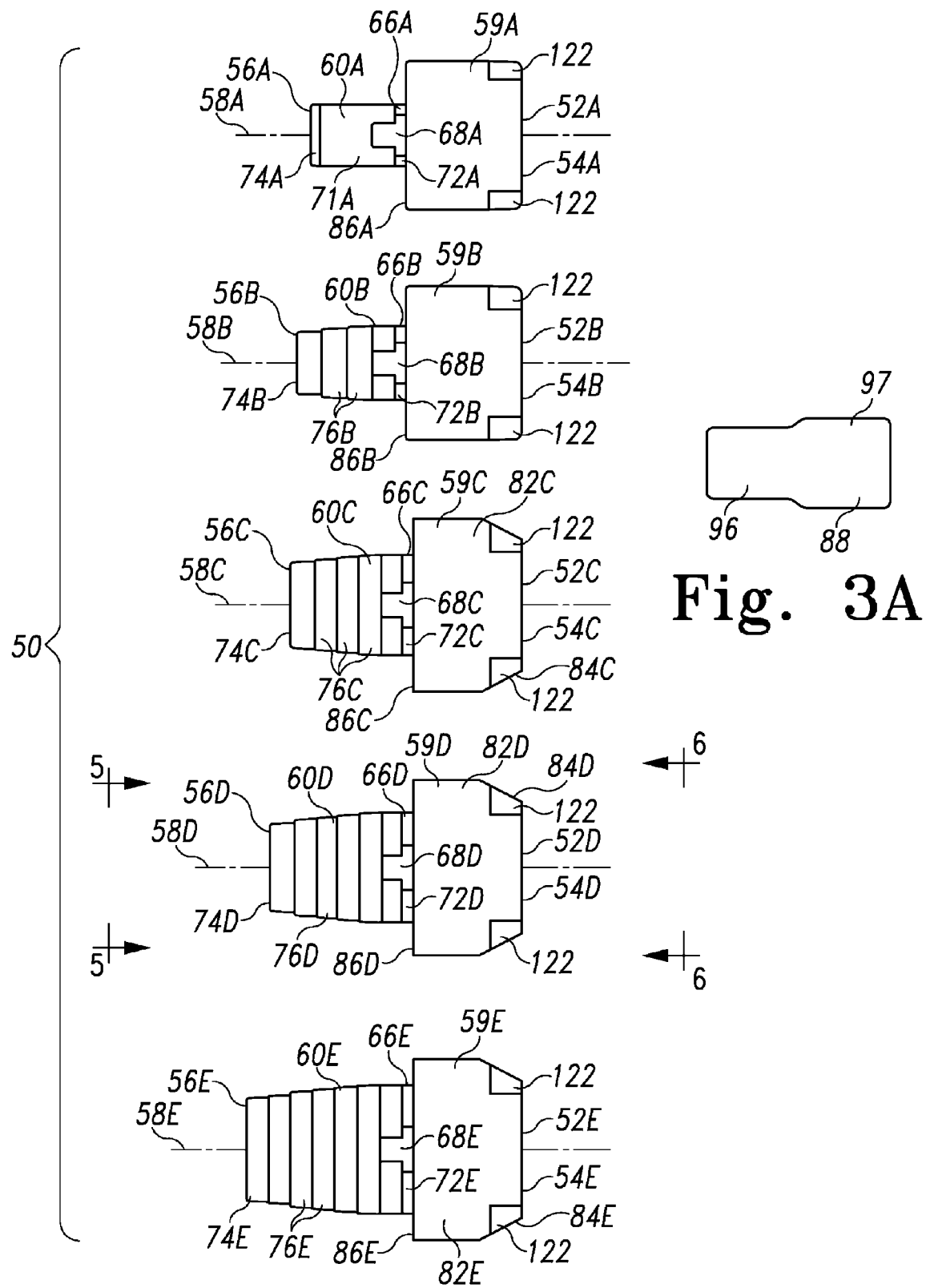
FIG. 3 is an elevation of a set of diaphyseal implant components of one embodiment of a set of orthopaedic implant components embodying the principles of the present invention.
FIG. 3A is an elevation of an adapter for use with the diaphyseal implant components of FIG. 3.

FIG. 3 illustrates a set 50 of diaphyseal implant components that can be used in the system or kit of the present invention. The illustrated set 50 of diaphyseal implant components includes five sizes of diaphyseal components, labeled 52A, 52B, 52C, 52D, 52E. The illustrated diaphyseal components 52A, 52B, 52C, 52D, 52E include several common features. In the following description and in the drawings, like parts are identified with the same reference number, followed by a letter designation to identify the particular size of component.

Each of the illustrated diaphyseal components 52A, 52B, 52C, 52D, 52E has a first end 54A, 54B, 54C, 54D, 54E a second end 56A, 56B, 56C, 56D, 56E and a longitudinal axis 58A, 58B, 58C, 58D, 58E extending from the first end 54A, 54B, 54C, 54D, 54E to the second end 56A, 56B, 56C, 56D, 56E. Each of the illustrated diaphyseal components 52A, 52B, 52C, 52D, 52E also has a collar portion 59A, 59B, 59C, 59D, 59E and a tapered outer surface 60A, 60B, 60C, 60D, 60E.

The tapered outer surface 60A, 60B, 60C, 60D, 60E of each diaphyseal implant component 52A, 52B, 52C, 52D, 52E in the set 50 is of a different size to accommodate the needs of the individual patient's anatomy. The illustrated set includes sizes ranging from extra-extra-small 52A to large 52E.

The tapered outer surface 60A, 60B, 60C, 60D, 60E of each diaphyseal implant component 52A, 52B, 52C, 52D, 52E in the set 50 has a minimum outer diameter at the second end 56A, 56B, 56C, 56D, 56E and a maximum outer diameter spaced from the first end 54A, 54B, 54C, 54D, 54E and the second end 56A, 56B, 56C, 56D, 56E. The maximum outer diameter is indicated at 66A, 66B, 66C, 66D, 66E in FIG. 3.

The tapered outer surface 60A, 60B, 60C, 60D, 60E, 60F may have a plurality of flats 68A, 68B, 68C, 68D, 68E at the maximum outer diameter 66A, 66B, 66C 66D, 66E. The flats may be provided to help to limit rotation of the diaphyseal components 52A, 52B, 52C, 52D, 52E with respect to the bone after implantation, as described in more detail below. It should be understood that the diaphyseal implant components could be provided without such flats if desired.

Figure 5:
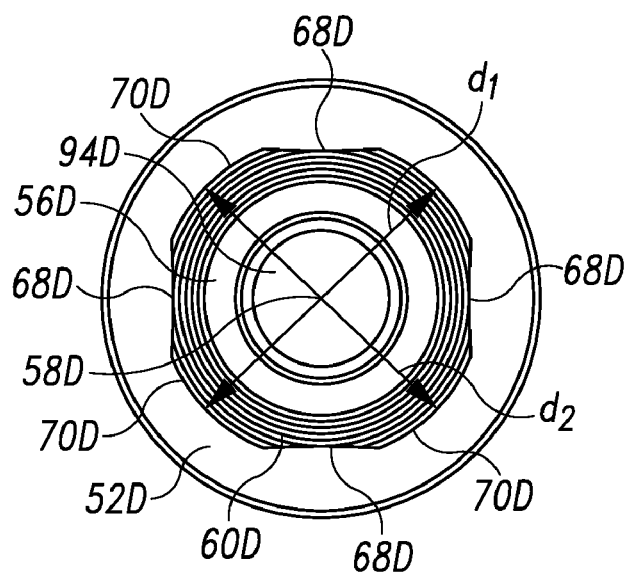
FIG. 5 is an end view of one of the diaphyseal implant components of FIGS. 3-4 taken along line 5-5 of FIG. 3.
Figure 6:
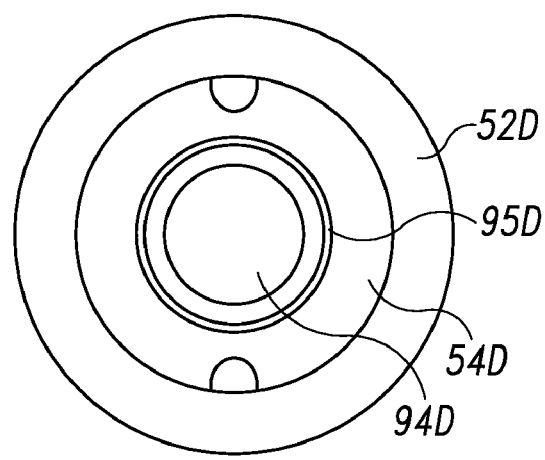
FIG. 6 is an end view of the diaphyseal implant component of FIG. 5, taken along line 6-6 of FIG. 3.

FIG. 5 illustrates an end view of one of the diaphyseal implant components 52D of the set 50, taken from the second end 56D of the component. As there shown, the tapered outer surface 60D has four equally spaced flats 68D connected by curved arcs 70D. The maximum outer dimensions of the tapered outer surface 60D are shown at $d_1$ and $d_2$ in FIG. 5; in the illustrated embodiments, $d_1=d_2$. Thus, the tapered outer surface 60D has the same outer dimension $d_1$, $d_2$ along two perpendicular transverse axes at the maximum outer dimension 66D of the tapered outer surface 60D.

In the smallest size of diaphyseal implant component 52A most of the tapered outer surface 60A has a frustoconical shape, shown at 71A in FIG. 3. Frustoconical is intended to mean shaped like the frustum of a cone, that is, it has the shape of the basal part of a solid cone formed by cutting off the top by a plane parallel to the base. The smallest illustrated diaphyseal implant component 52A also has a first annular step 72A and a last annular step 74A. In each of the other sizes of diaphyseal implant components 52B, 52C, 52D, 52E in the set 50, the tapered outer surface 60B, 60C, 60D, 60E comprises a plurality of annular steps: there is a first step 72B, 72C, 72D, 72E between the first end 54B, 54C, 54D, 54E and second end 56B, 56C, 56D, 56E of the diaphyseal implant components, a last annular step 74A, 74C, 74D, 74E at the second end 56B, 56C, 56D, 56E of the diaphyseal implant component and a plurality of intermediate steps 76B, 76C, 76D, 76E between the first step 72B, 72C, 72D, 72E and last step 74A,74C, 74D, 74E.

Each step has a substantially cylindrically shaped outer surface and a longitudinal height; the largest diameter steps deviate from a cylindrical shape in the illustrated embodiments because of the presence of the four flats 68.

In each illustrated size of diaphyseal implant component, the first annular step 72A, 72B, 72C, 72D, 72E has the greatest maximum outer diameter, and the maximum outer diameter of each step progressively decreases to the last annular step 74A, 74A, 74C, 74D, 74E which has the smallest maximum outer diameter. In the illustrated set of diaphyseal implant components 52A, 52B, 52C, 52D, 52E examples of sizes and numbers of steps are provided in the following table:

Extra Extra Small Diaphyseal Implant Component 52A

|  | Height | Outer Diameter | Taper Angle |
|---|---|---|---|
| First step 72A | 2 mm | 12.95 mm | — |
| Frustoconical Portion 71A | 15.04 mm | 12.65 mm maximum to 10.67 mm minimum | 3° |
| Last Step 74A | 2 mm | 9.81 mm | — |

Extra Small Diaphyseal Implant Component 52B

|  | Step Height | Step Outer Diameter | Overall Taper Angle |
|---|---|---|---|
| First step 72B | 2 mm | 15.23 mm | 4°52' |
| Second step | 4 mm | 14.37 mm |  |
| Third step | 4 mm | 13.51 mm |  |
| Fourth step | 4 mm | 12.65 mm |  |
| Last step 74B | 4 mm | 11.79 mm |  |

Small Diaphyseal Implant Component 52C

|  | Step Height | Step Outer Diameter | Overall Taper Angle |
|---|---|---|---|
| First step 72C | 2 mm | 19.09 mm | 4°33' |
| Second step | 4 mm | 18.37 mm |  |
| Third step | 4 mm | 17.65 mm |  |
| Fourth step | 4 mm | 16.93 mm |  |
| Fifth step | 4 mm | 16.21 mm |  |
| Last step 74C | 4 mm | 15.49 mm |  |

Medium Diaphyseal Implant Component 52D

|  | Step Height | Step Outer Diameter | Overall Taper Angle |
|---|---|---|---|
| First step 72D | 2 mm | 22.53 mm | 6°35' |
| Second step | 4 mm | 21.51 mm |  |
| Third step | 4 mm | 20.49 mm |  |
| Fourth step | 4 mm | 19.47 mm |  |
| Fifth step | 4 mm | 18.45 mm |  |
| Sixth step | 4 mm | 17.43 mm |  |
| Last step 74D | 4 mm | 16.41 mm |  |

Large Diaphyseal Implant Component 52E

|  | Step Height | Step Outer Diameter | Overall Taper Angle |
|---|---|---|---|
| First step 72E | 2 mm | 26.51 mm | 6°39' |
| Second step | 4 mm | 25.49 mm |  |
| Third step | 4 mm | 24.47 mm |  |
| Fourth step | 4 mm | 23.45 mm |  |
| Fifth step | 4 mm | 22.44 mm |  |
| Sixth step | 4 mm | 21.42 mm |  |
| Seventh step | 4 mm | 20.40 mm |  |
| Last step 74E | 4 mm | 19.38 mm |  |

In the above table, the Overall Taper Angle refers to the angle defined by a line tangent to the steps 72, 74, 76 and a line parallel to the longitudinal axis 58 in each size.

It should be understood that the sizes, numbers of steps and overall taper angles identified in the above tables are provided as examples only. The present invention is not limited to a stepped configuration or to any particular size, number of steps or overall angle of taper unless expressly called for in the claims. Moreover, although five sizes are illustrated in the set 50, fewer or more sizes could be provided; the invention is not limited to any number of sizes of implant components in a set unless expressly called for in the claims.

In each of the illustrated diaphyseal implant components 52A, 52B, 52C, 52D, 52E, most of the tapered outer surface is porous: the frustoconical portion 71A of the small diaphyseal implant component 52A and its first step 72A are porous and all of the first and intermediate steps 72B, 72C, 72D, 72E, 76B, 76C, 76D, 76E of the other sizes of diaphyseal implant components 52B, 52C, 52D, 52E are porous. The last or smallest diameter step 74 in each size is not porous in the illustrated embodiment.

As used herein, "porous" refers to a surface that is conducive to bone ingrowth for non-cemented fixation, and "smooth" refers to a surface that is not conducive to such bone ingrowth. Suitable porous surfaces can be made by many different methods: casting, embossing, etching, milling, machining, and coating such as by plasma-spraying or by bonding, for example. Bonded materials can comprise sintered metal beads, sintered metal mesh or screen, or sintered metal fibers, for example. Known, commercially available materials and techniques can be used to create the porous surfaces of the diaphyseal components: for example, POROCOAT® coating, available from DePuy Orthopaedics, Inc. of Warsaw, Ind., could be used, as well as other commercially available coatings. In addition, the porous surfaces may include other materials conducive to bone ingrowth, such as hydroxy apatite coatings, for example. It should be understood that the above-identified examples of materials, methods and commercial products are provided as examples only; the present invention is not limited to any particular material, method or commercial product for the porous surfaces unless expressly called for in the claims. In addition, it should be understood that as additional materials and methods become available to create surfaces that promote bony ingrowth, it is believed that such other materials and methods may also be useful with the present invention.

Each of the illustrated flats 68A, 68B, 68C, 68D, 68E in the illustrated diaphyseal implant components is 6 mm high. The flats are disposed at 90° intervals around the first step and second step in the diaphyseal implant components 52B, 52C, 52D, 52E that have stepped tapered outer surfaces 60B, 60C, 60D, 60E and are also disposed at 90° intervals around the tapered frustoconical surface 71A and first step 72A of the smallest diaphyseal implant component 52A. It should be understood that the flats may have different dimensions and different positions.

In each size of diaphyseal implant component illustrated in FIG. 3, the largest diameter portion 66A, 66B, 66C, 66D, 66E of the tapered outer surface 60A, 60B, 60C, 60D, 60E is adjacent to the annular collar 59A, 59B, 59C, 59D, 59E. The annular collars 59A, 59B, 59C, 59D, 59E have outer diameters greater than the maximum outer diameter 66A, 66B, 66C, 66D, 66E of the tapered outer surface 60A, 60B, 60C, 60D, 60E. In ea of the illustrated sizes, at least a portion of the outer surface of each collar is cylindrical in shape: in the extra extra small component 52A and extra small component 52B, all or substantially all of the outer surface of the collar 59A is cylindrical in shape; in the other larger sizes 52C, 52D, 52E the collars 59C, 59D, 59E include a cylindrical portion 82C, 82D, 82E adjacent to the tapered outer surface 60C, 60D, 60E and a frustoconical portion 84C, 84D, 84E at the first end 54C, 54D, 54E. A portion or all of each collar 59A, 59B, 59C, 59D, 59E may be porous; for example, an annular porous strip having a height (longitudinal dimension) of 10 mm may be provided on the cylindrical portions 82A. 82B, 82C, 82D, 82E for soft tissue attachment and ingrowth. Variations in the type and characteristics of the porous coating may be made to encourage soft tissue ingrowth, as opposed to bone ingrowth. Moreover, features may be included on the collar to allow for attachment of soft tissue or the periosteum; for example, suture holes may be provided. Preferably, a portion of each collar portion has a surface that is conducive to ingrowth of the periosteum.

Each collar 59A, 59B, 59C, 59D, 59E includes a transverse annular surface 86A, 86B, 86C, 86D, 86E that is perpendicular to the longitudinal axis 58A, 58B, 59C, 58D, 58E of the diaphyseal implant component. The transverse annular surfaces 86A, 86B, 86C, 86D, 86E are sized and provide surface areas sufficient to bear against the resected end of the bone if the diaphyseal implant component subsides. For example, the transverse annular surface 86A, 86B, 86C, 86D, 86E may have an outer diameter in the range of about 1 inch to 1½ inch (25.4 mm to 38.1 mm) and an inner diameter at the first step 72A, 72B, 72C, 72D, 72E in the range of about ½ inch to 1 inch (12.7 mm to 25.4 mm), thus providing surface areas in the range of about 0.59 square inches to about 0.98 square inches (about 380 $mm^2$ to about 633 $mm^2$). With a porous coating, the diameters should increase by about sixty-thousandths of an inch (1.5 mm) It should be understood that these dimensions are provided as examples only; the present invention is not limited to any particular dimension unless expressly called for in the claims. The transverse annular surface 86A, 86B, 86C, 86D, 86E may be porous or smooth; if porous, the transverse annular surface may provide a surface conducive to tissue ingrowth. It may be desirable to limit any porous coating to the outer portions of the transverse annular surface.

The diaphyseal implant components 52A, 52B, 52C, 52D, 52E may be used with an adapter 88 shown in FIGS. 3A and 4A and described in more detail below.

Figures 4, 4A:
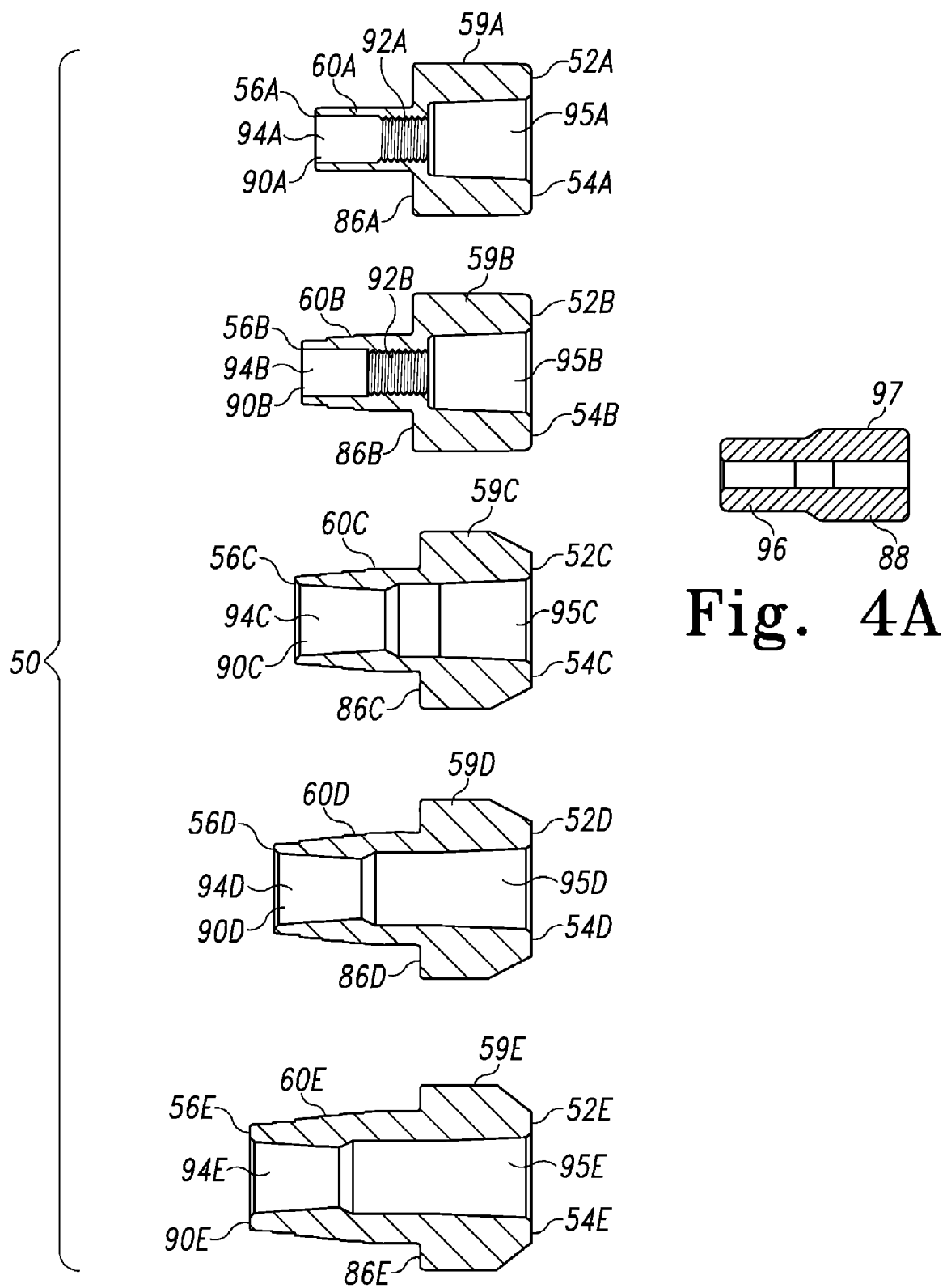
FIG. 4 is a longitudinal cross-section of the set of diaphyseal implant components of FIG. 3.
FIG. 4A is a longitudinal cross-section of the adapter of FIG. 3A.
Figure 7:
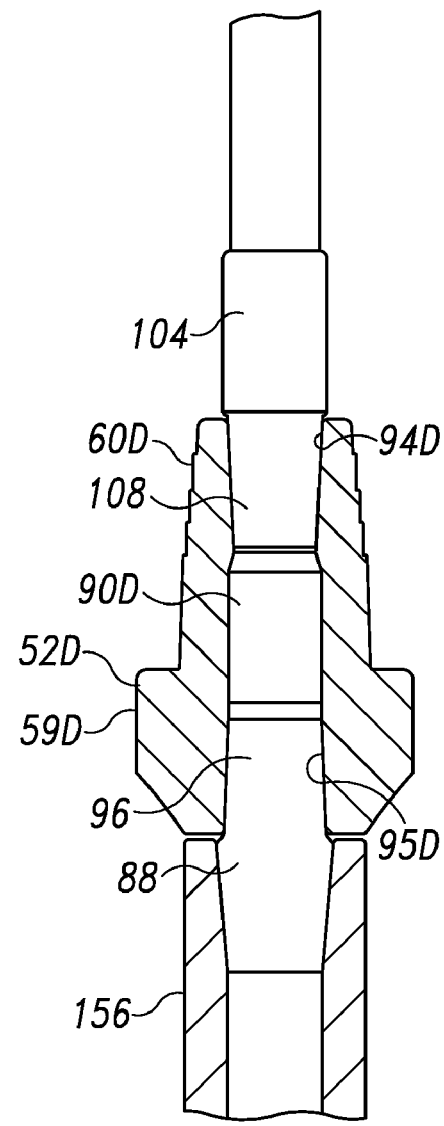
FIG. 7 is an elevation of one of the diaphyseal implant components of FIGS. 3-4, assembled with the adapter of FIGS. 3-4 and with a stem extension and intercalary implant component, shown with the diaphyseal implant component and intercalary implant component in longitudinal cross-section.

Representative cross-sections of the diaphyseal implant components 52A, 52B, 52C, 52D, 52E are illustrated in FIG. 4. Each of the diaphyseal implant components 52A, 52B, 52C, 52D, 52E has a throughbore 90A, 90B, 90C, 90D, 90E extending longitudinally through the entire length of the component, from the first end 54A, 54B, 54C, 54D, 54E to the second end 56A, 56B, 56C, 56D, 56E. In the extra-small and small sizes 52A, 52B, the throughbore 90A, 90B has a threaded portion shown at 92A and 92B in FIG. 4 to receive the threaded end 114 (shown in FIG. 9) of a stem extension 110. In the other larger sizes 52C, 52D, 52E of diaphyseal implant components, the portion of the throughbore 90C, 90D, 90E near the second end 56C, 56D, 56E comprises a Morse taper bore 94C, 94D, 94E sized and shaped to receive a Morse taper post 108 at the end of a stem extension 104 or at the end of an adapter. In all of the illustrated diaphyseal implant components, the portion of the throughbore 90A, 90B, 90C, 90D, 90E near the first end 54A, 54B, 54C, 54D, 54E comprises a larger size Morse taper bore 95A, 95B, 95C, 95D, 95E sized and shaped to receive a Morse taper post 96 at one end of the adapter 88. In the larger sizes of diaphyseal implant components, the smaller Morse taper bores 94C, 94D, 94E are co-axial with and connected to the larger Morse taper bores 95C, 95D, 95E by a transition portion and a cylindrical portion. FIG. 7 illustrates one of the diaphyseal implant components 52D in cross-section, assembled with an adapter 88, segmental implant component 102 and stem extension 104; both ends 54D, 56D are suitable for connection to other implant components. It should be understood that the illustrated longitudinal throughbores are provided as examples only; other designs could be employed, depending on the desired wall thickness for the implant and the type of connection to be employed to the other implant components.

Figures 8, 9:
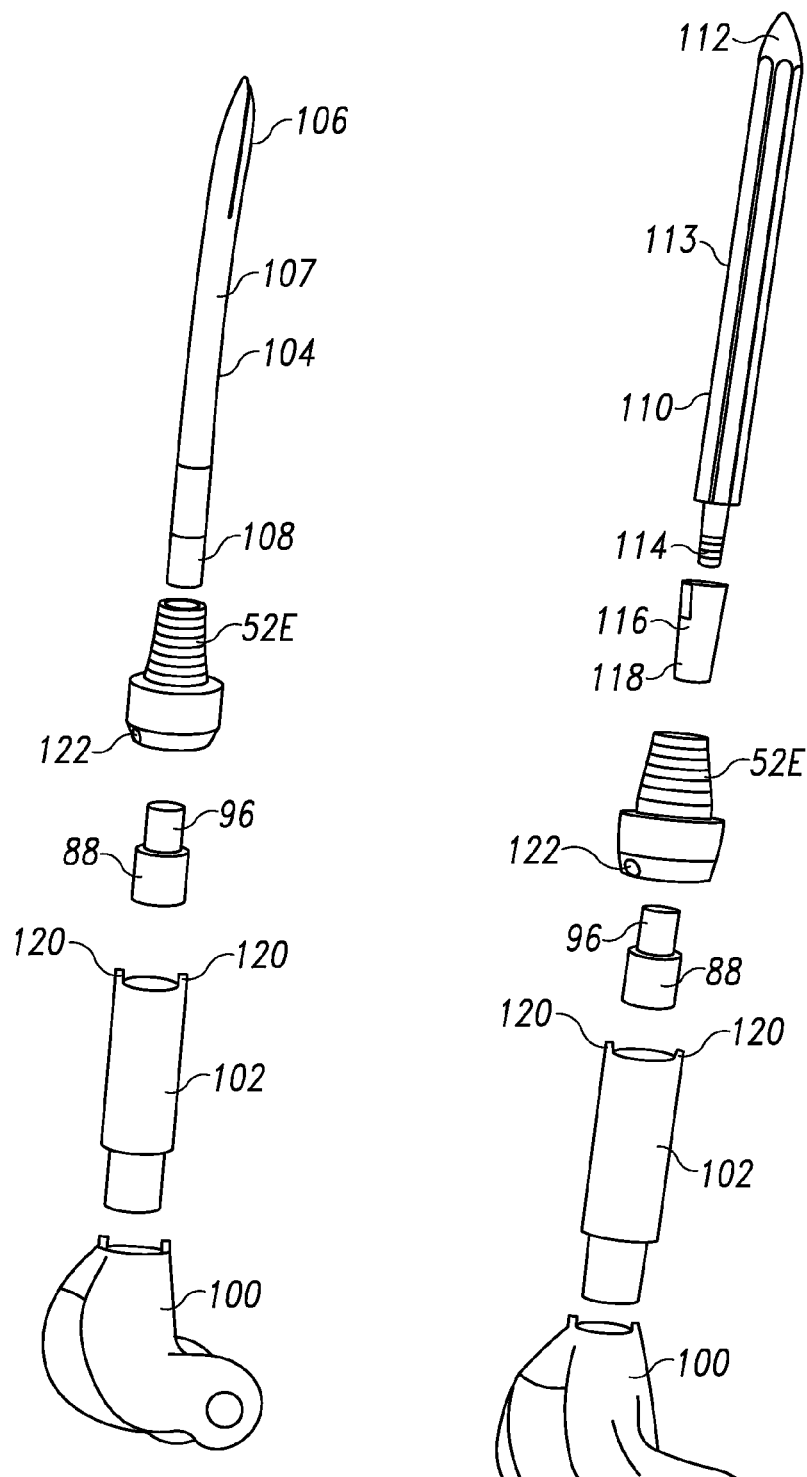
FIG. 8 is an exploded perspective view of a distal femoral implant assembly illustrating use of one of the diaphyseal implant components of FIGS. 3-4 in use with an adapter and one style of stem extension.
FIG. 9 is an exploded perspective view similar to FIG. 8, but illustrating use of one of the diaphyseal implant components of FIGS. 3-4 in use with an adapter and a different style of stem extension.

FIGS. 8-9 illustrate the large size diaphyseal implant component 52E in exploded views with other modular implant components that may be included in a kit or system and assembled with the diaphyseal implant component 52E for implantation. In FIGS. 8-9, the assembly is intended for use in replacing a portion of the distal femur. The assemblies of both FIGS. 8 and 9 include a distal femoral implant 100, a segmental implant component 102, a diaphyseal implant component 52E, adapters 88, 116 and a stem extension. Features of the adapter 116 are disclosed in more detail in U.S. patent application Ser. No. 10/817,051 entitled "Modular Implant System with Fully Porous Coated Sleeve", filed on Apr. 2, 2004 by Goodfried, Hazebrouck, Lester and Brown (U.S. Pat. Publication No. US2005/0107883A1), the complete disclosure of which is incorporated by reference herein.

In FIG. 8, the stem extension 104 has a coronal-slotted free end or tip 106, a body 107 and a connection end 108. The connection end 108 comprises a Morse taper post in the embodiment of FIG. 8. The Morse taper post at the connection end 108 is received within and frictionally locks with the Morse taper bore 94E of the diaphyseal implant component 52E. In FIG. 9, the stem extension 110 has a free end or tip 112, a body 113 and a connection end 114 that comprises a male threaded member. The embodiment of FIG. 9 also includes an adapter 116 with a threaded opening (not shown) to receive the male threaded connection end 114 of the stem extension and a Morse taper post 118 to be received in the Morse taper bore 94E of the diaphyseal implant component 52E. All of the large size diaphyseal implant components 52C, 52D, 52E can be assembled with stem extensions in the manners illustrated in FIGS. 8-9. Due to constraints on the thicknesses of the walls of the tapered outer surfaces 60A, 60B of the smaller sized diaphyseal implant components 52A, 52B, accommodation is only made for connection to a stem extension with a threaded male end of the type shown in FIG. 9.

The bodies 107, 113 of the stem extensions 104, 110 may vary. For example, a substantial part of the length of the body, such as body 107 of FIG. 8, can be porous. Alternatively, the body can be sized and shaped for cemented application, like the body 113 of the stem extension 110 of FIG. 9. Alternatively, the body of the stem extension can be splined.

Figure 10:
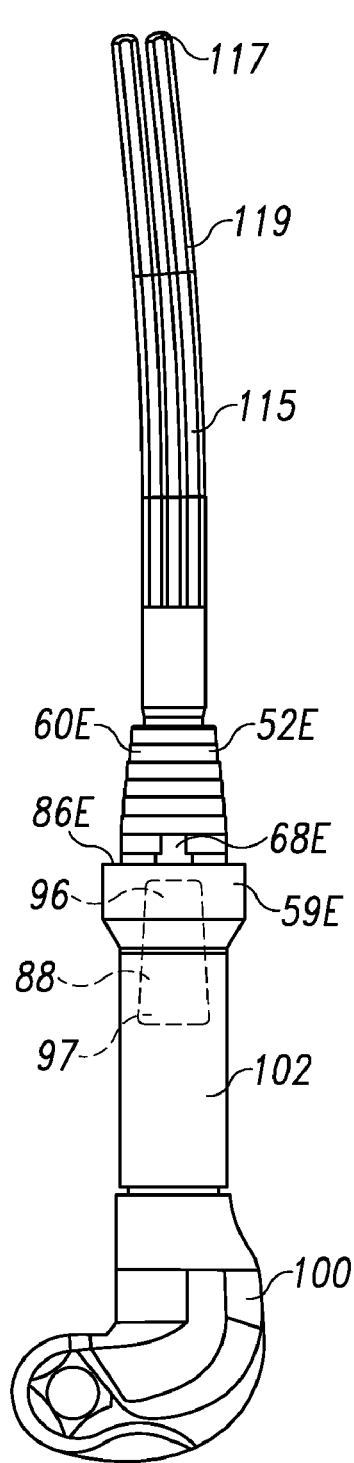
FIG. 10 is a side view of a distal femoral implant assembly including one of the diaphyseal implant components and adapter of FIGS. 3-4 in use with a different style of stem extension.
Figure 11:
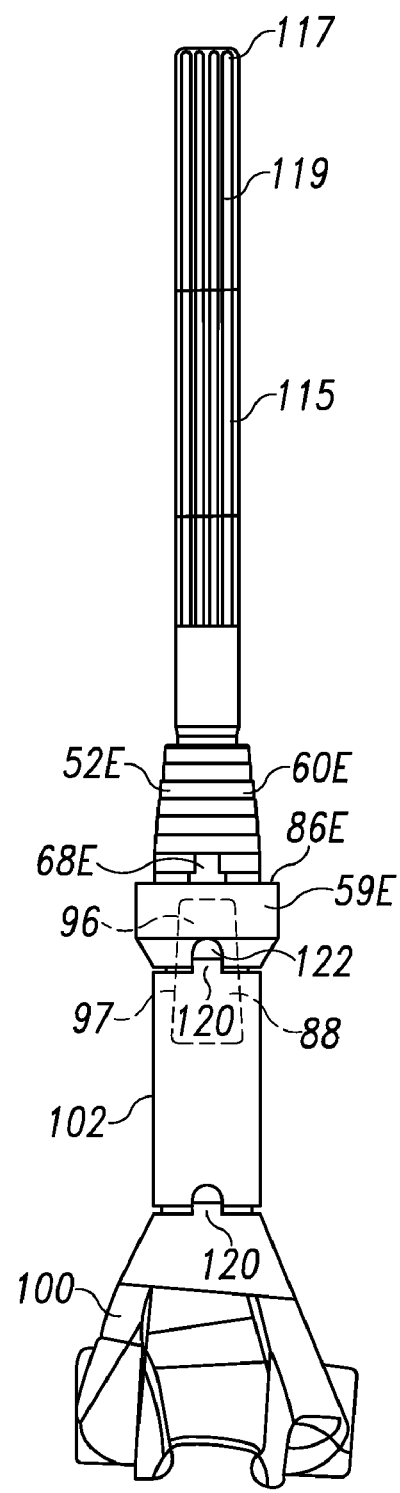
FIG. 11 is an anterior view of the distal femoral implant assembly of FIG. 10.

FIGS. 10-11 illustrate a stem extension 115 with a coronal slotted free end 117, a splined body 119, and a connection end (not shown) comprising a Morse taper post. In the embodiment of FIGS. 10-11, the splined body 119 of the stem extension 115 comprises a plurality of cutting flutes. The stem extension 115 of FIGS. 10-11 is not porous. Although in FIGS. 10-11 the free end 117 of the stem extension 115 is illustrated as being substantially flat, it may be desirable for the free end 117 to be bullet-shaped.

As illustrated in phantom FIGS. 10-11, the adapter 88 includes a second Morse taper post 97, longitudinally aligned with the first Morse taper post 96. As shown in FIG. 4A, the adapter also includes a throughbore 99 for pressure relief. The second Morse taper post 97 is sized and shaped to be received within and frictionally lock with a Morse taper bore formed in the femoral component 100, segmental component 102 or other implant component. U.S. Pat. Publication No. US2003/0204267A1, which is incorporated by reference herein in its entirety, discloses additional details regarding the Morse taper bores in the femoral and segmental components, and of appropriate Morse taper posts for use with such components.

As disclosed in U.S. Pat. Publication No. US2003/0204267A1, the distal femoral implant component 100 and segmental component 102 both include tabs 120. Each of the diaphyseal implant components 52A, 52B, 52C, 52D, 52E include corresponding notches 122 to receive the tabs 120 to prevent the diaphyseal implant components from rotating. These notches can also be used to separate the components if necessary; a tool such as that disclosed in U.S. Pat. No. 6,786,931 may be used.

It should be understood that a typical implant kit or system would include several sizes of distal femoral implant components 100, segmental components 102 and stem extensions 104, 110. It should also be understood that depending on the size and shape of the distal femoral component, it may not be necessary to use a segmental component 102; the diaphyseal implant component 52A, 52B, 52C, 52D, 52E and adapter 88 could be connected directly to the femoral implant component 100.

Use of the diaphyseal implant components 52A, 52B, 52C, 52D, 52E of the present invention is not limited to segmental components and femoral components. As illustrated in FIGS. 12-15, the diaphyseal implant components of the present invention can be used with other implant components having an articulation portion. For example, as shown in FIG. 12, the articulation portion of the implant component could comprise a proximal femoral component 150 (including a femoral head 152). As shown in FIG. 13 the articulation portion of the implant component could comprise a proximal tibia component 154 or other component, such as a proximal humeral component (not shown).

Figure 14:
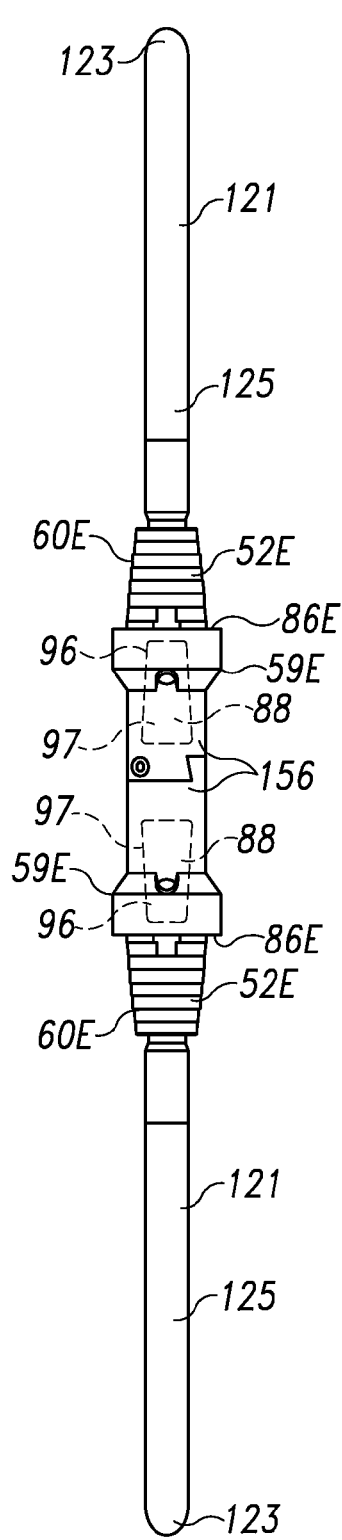
FIG. 14 is a side view of an intercalary implant assembly including two of the diaphyseal implant components and two of the adapters of FIGS. 3-4.
Figure 15:
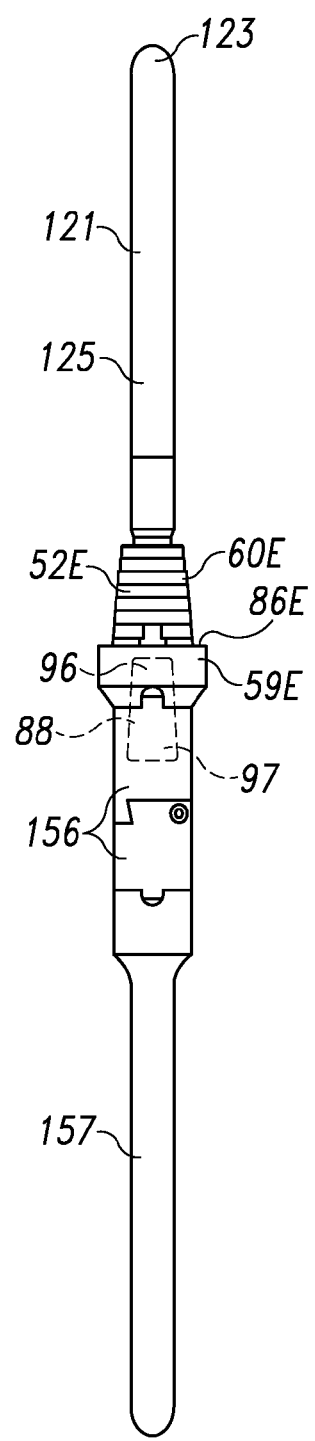
FIG. 15 is a side view of an intercalary implant assembly including one of the diaphyseal implant components and adapter of FIGS. 3-4.

As shown in FIGS. 14-15, the implant component could be an intercalary implant instead of an articulation component. FIG. 14 illustrates two large size diaphyseal implant components 52E in use with a two-piece intercalary implant 156 of the type disclosed in U.S. application Ser. No. 10/403,612 entitled "Intercalary Prosthesis, Kit and Method," filed Mar. 31, 2003 by Hazebrouck (U.S. Pat. Publication No. US2004/0193268A1), incorporated by reference herein in its entirety, or those disclosed in U.S. application Ser. No. Ser. No. 10/403,357 entitled "Intercalary Implant," filed on Mar. 31, 2003 by Natalie Heck and Michael C. Jones (U.S. Pat. Publication No. US2004/0193267A1) (also incorporated by reference herein in its entirety). Such implants may be used with intercalary trials such as those disclosed in U.S. patent application Ser. No. 10/952,581, entitled "Orthopaedic Spacer," filed on Sep. 24, 2004 by Hazebrouck, the complete disclosure of which is incorporated by reference herein. FIG. 15 illustrates a single diaphyseal implant components in use with the two-piece intercalary component 156 and a standard stem extension 157 for the LPS implant system.

In FIGS. 12-15 the stem extension is shown diagrammatically and indicated generally by reference number 121, with the free end indicated by reference number 123. Other than the bullet shape of the free end 123, no other features are shown for the body 125 of the stem extension. It should be understood that the body 125 of the stem extension 121 in any of FIGS. 12-15 could have any of the above described features, such as splined cutting flutes, a porous coating, a coronally slotted free end, or could be designed for cemented application.

All of the components of the illustrated implant systems can be made of standard materials for such implants, such as titanium and cobalt-chrome alloys.

It should be understood that although the principles of the present invention are described and illustrated with reference to implant components available from DePuy Orthopaedics, Inc., the invention is not limited to these components or their features. The principles of the present invention can be applied to other implant components, including those of other manufacturers and those subsequently developed.

Figure 16:
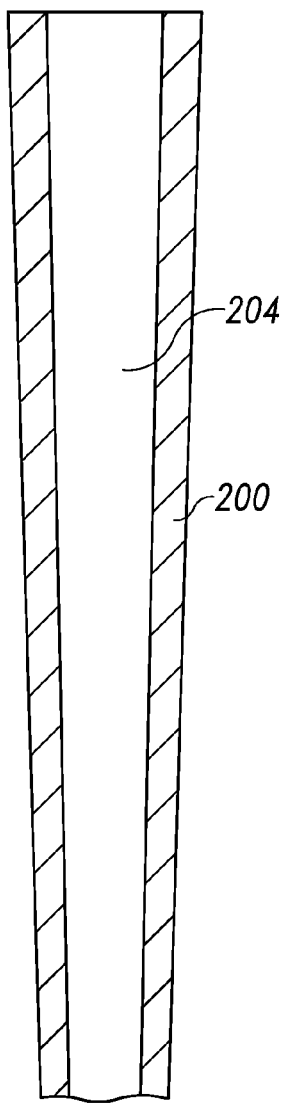
FIG. 16 is a diagrammatic cross-section of a portion of the remaining portion of the diaphysis after a portion of the femur or long bone has been resected.
Figure 17:
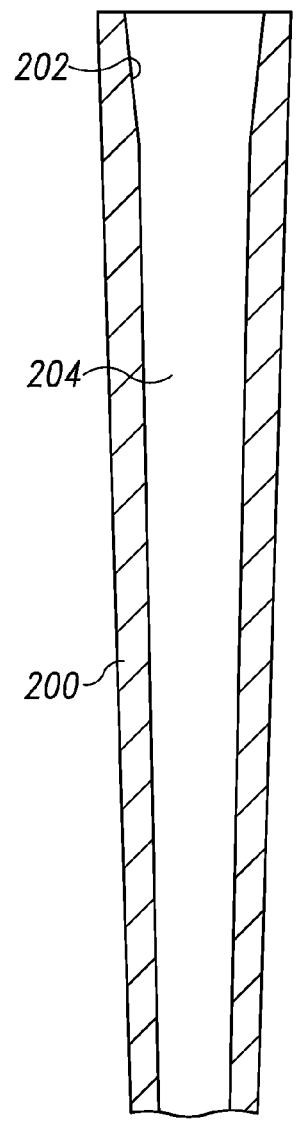
FIG. 17 illustrates the remaining resected diaphysis of FIG. 16 after a tapered bore has been prepared at the resection site of the bone.
Figure 18:
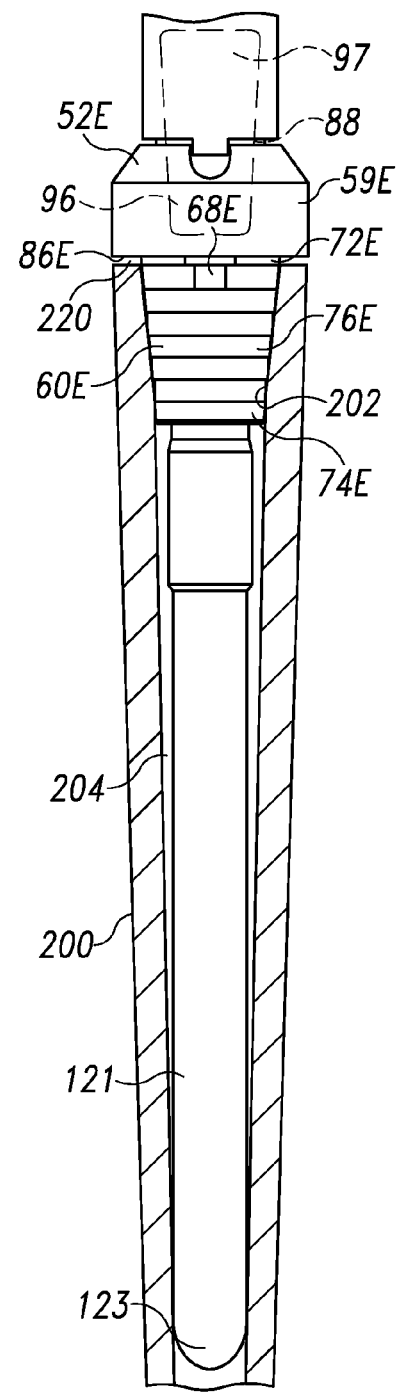
FIG. 18 illustrates the remaining resected diaphysis of FIG. 17 with an implant assembly including a diaphyseal implant component fully seated in the bone.

In use, depending on the condition of the native bone tissue, the orthopaedic surgeon will determine the amount of bone to be resected from the femur (or other long bone). Commercially available instrumentation can be used to resect the bone in the appropriate manner. The diaphysis of a resected bone is illustrated in FIGS. 16-18 at 200. If it is desirable to use a diaphyseal implant component 52A, 52B, 52C, 52D, 52E to secure the implant in place, the surgeon can then select an appropriate size of diaphyseal implant component 52A, 52B, 52C, 52D or 52E for the individual patient. The diaphysis 200 of the bone can then be prepared to receive the selected diaphyseal implant component 52A, 52B, 52C, 52D or 52E. The surgeon can use a conical reamer (not shown) of a size and shape matching the size and shape of the selected diaphyseal component to mill or machine the diaphysis 200 of the bone to create a tapered bore that closely matches the size and shape of the tapered outer surface 60A, 60B, 60C, 60D, 60E of the selected diaphyseal implant component. A tapered bore is illustrated in FIGS. 17-18 at 202. Since the tapered bore is created to match the size and shape of the selected diaphyseal implant component, the implants and techniques of the present invention are adaptable to different patient anatomies.

The stem extension and part of the diaphyseal implant component of the assembled implant, can then be inserted into the bone as illustrated in FIG. 18 and positioned with the tip or free end of the stem extension engaging the bone surface of the intramedullary canal 204 and with the tapered outer surface 60A, 60B, 60C, 60D or 60E bearing against the tapered diaphyseal bone defining the tapered bore 202. The stem extension in FIG. 18 is identified with reference number 121 and its free end is identified with reference number 123; as discussed above with respect to FIGS. 12-15, the stem extension 121 is illustrated diagrammatically, and can include any of the features of the stem extensions 104, 110, 115 described above. Because of the shapes and textures of the implant components 121, 52A, 52B, 52C, 52D or 52E, there should be no binding before the diaphyseal component 52A, 52B, 52C, 52D or 52E is fully seated. Accordingly, implantation should be relatively easy.

Generally, when implanted, the first step 72A, 72B, 72C, 72D, 72E of each of the diaphyseal implant components 52A, 52B, 52C, 52D, 52E will be exposed outside of the bone as shown in FIG. 18. Subsequently, some subsidence of the implant can occur over time without damage to the bone. The flats 68E prevent the diaphyseal component 52E from rotating or turning in the tapered bore 202 that the surgeon created for it.

As shown in FIG. 18, when fully seated, the implant assembly contacts the bone at both the tip 123 of the stem extension 121 and at the tapered outer surface 60E of the diaphyseal component 52E. Bone ingrowth can occur around the entire tapered outer surface 60E of the diaphyseal implant component 52E. Depending on the intramedullary canal anatomy and characteristics of the stem extension, bone ingrowth can also occur along all or part of the body of the stem; for example, bone ingrowth could occur at the free end of the stem extension and/or at any area between the diaphyseal component and the free end of the stem. For example, if a cemented stem extension is used, such as the stem extension 110 of FIG. 9, there should be no bone ingrowth along the body of the stem. Similarly, no substantial bone ingrowth should occur along the stem with the splined stem extension 115 of FIGS. 10-11. If all or part of the stem extension 104 of FIG. 8 is porous, bone ingrowth can be expected at the porous area.

With the stepped designs of the larger diaphyseal implant components, such as diaphyseal implant components 52B, 52C, 52D, 52E, shear forces are essentially converted to compressive loads, and the compressive loads are spread among the steps 74, 76 contacting the diaphyseal bone defining the tapered bore 202. Accordingly, the implant is immediately stable and capable of bearing weight. In addition, with the bone bearing the axial load at the tapered bore 202, there is no disadvantageous stress shielding of the bone. Moreover, with the implant assembly contacting the bone at both the tip 106 of the stem extension and at the contacting surfaces diaphyseal bone defining the tapered bore 202 and tapered outer surface 60, any moment arm is significantly reduced if not eliminated. With bone ingrowth occurring at both spaced locations over time, long term implant stability should be improved. Accordingly, the implant assembly of the present invention should be less likely to loosen over time.

As can be seen in FIG. 18, there is a small gap 220 between the exposed resected bone surface and the transverse annular surface 86E of the collar 59E when implanted. If the implant does subside, this gap can decrease to the point that the transverse annular surface 86E bears directly against the exposed resected bone surface. If the transverse annular surface is porous, tissue ingrowth can occur in the gap 220 over time to seal the intramedullary canal 204 against debris.

With any of the illustrated diaphyseal implant components, the periosteum of the bone should grow into the porous outer surface of the collar portion 59A, 59B, 59C, 59D, 59E of the diaphyseal implant component 52A, 52B, 52C, 52D, 52E. Essentially, the ingrowth of tissue along the cylindrical outer surface of the collar portion (or along the exposed portion of the transverse annular surface 86A, 86B, 86C, 86D, 86E of the collar portion) should effectively seal off the intramedullary canal, to thereby protect the patient from injury or disease resulting from debris entering into the intramedullary canal.

With the modular implant system of the present invention, it should be possible to reduce inventory of the necessary parts in an implant system or kit.

It should also be understood that a typical surgical kit would also include trial implant components (not shown) like those shown in FIGS. 3-4 and 8-15. The surgeon would typically assemble a trial implant and temporarily secure the trial implant assembly in place on the prepared diaphyseal bone to ensure that the assembled implant will be the optimum for the individual patient's needs. The trial components can have features like those described above for the final implant components.

In case it is necessary to ultimately remove the implant assembly from the patient, such removal should not require the removal of excessive bone stock, since it should only be necessary to remove the portion of the diaphysis defining the tapered bore 202.

Various modifications and additions can be made to the above-described embodiments without departing from spirit of the invention. All such modifications and additions are intended to fall within the scope of the claims unless the claims expressly call for a specific construction.

We claim:

1. An orthopaedic implant kit for replacing a portion of a long bone, the long bone having an articulation portion, a diaphysis and an intramedullary canal, the kit including:

a plurality of modular articulation components shaped and sized to replace the articulation portion of the long bone, each modular articulation component including a tapered bore;

a plurality of modular stems to be received in the intramedullary canal of the long bone, each stem having a free end and an opposite end capable of being connected to another implant component;

an adapter having a first end and a second end, a first tapered post sized and shaped to be complementary to the tapered bore of at least one of the articulation components for connecting the adapter to the articulation component through frictional engagement of the first tapered post of the adapter and tapered bore of the articulation component, the first tapered post having its minimum outer dimension at the first end and its maximum outer dimension between the first and second ends, the adapter further comprising a second tapered post having its minimum outer dimension at the second end and its maximum outer dimension between the first and second ends, the first and second posts being longitudinally aligned along a common longitudinal axis;

a plurality of modular diaphyseal implant components capable of being connected to the modular stems, each diaphyseal implant component including:

a first end having a tapered bore sized and shaped to be complementary to the second tapered post of the adapter for connecting the diaphyseal component to the adapter through frictional engagement of the second tapered post of the adapter and tapered bore of the diaphyseal implant component;

a second end for connection to a selected modular stem, said second end having a bore co-axial with the tapered bore of the first end of the diaphyseal implant component;

a longitudinal axis extending between the first ( ) and the second ends of the diaphyseal implant component;

a porous tapered outer surface having a minimum outer dimension at the second end and a maximum outer dimension positioned between the first ( ) and the second ends of the diaphyseal implant component, the tapered outer surface of the diaphyseal component having the same maximum outer transverse outer dimension along two perpendicular axes; and a collar adjacent to the porous tapered outer surface, the collar including an annular surface adjacent to the porous tapered outer surface, a cylindrical portion extending from the annular surface toward the first end of the diaphyseal implant component, and a frusto-conical portion extending from the cylindrical portion to the first end of the diaphyseal implant component, the tapered bore extending through the frusto-conical portion, the annular surface of the collar being transverse to the longitudinal axis of the diaphyseal implant component, the annular surface of the collar having a maximum outer dimension greater than the maximum outer dimension of the porous tapered outer surface;

wherein:

the porous tapered outer surface of each diaphyseal implant component comprises a plurality of steps, each step having a height, an outer dimension and an annular surface perpendicular to the longitudinal axis of the diaphyseal implant component;

the maximum outer diameter of the annular surface of the collar defines the maximum outer dimension of the diaphyseal implant component;

the annular surface of the collar has the same maximum outer transverse dimension along two perpendicular axes;

the maximum outer transverse dimension of the frusto-conical portion of the collar at the first end of the diaphyseal implant component is less than the maximum outer transverse dimension of the annular surface of the collar; and the maximum outer transverse dimension of the annular surface of the collar is the same as the maximum outer transverse dimension of the cylindrical portion of the collar.

2. The kit of claim 1 wherein the plurality of steps of the porous tapered outer surface includes a first step adjacent to the annular surface of the collar, the first step having the smallest height and largest outer dimension of all the steps.

3. The kit of claim 2 wherein said plurality of steps include steps having cylindrically-shaped outer surfaces.

4. The kit of claim 1 further comprising a plurality of intercalary implant components shaped to replace a segment of the diaphysis of the long bone.

5. The kit of claim 1 wherein ( ) said plurality of steps include a plurality of flats parallel to the longitudinal axis of the diaphyseal implant component.

* * * * *